United States Patent
Zhou et al.

(10) Patent No.: US 11,766,577 B2
(45) Date of Patent: Sep. 26, 2023

(54) FLEXIBLE VARIABLE FREQUENCY ULTRASONIC THERAPEUTIC PROBE BASED ON THERMOACOUSTIC EFFECT OF CARBON NANOTUBE FILM

(71) Applicant: DALIAN UNIVERSITY OF TECHNOLOGY, Dalian (CN)

(72) Inventors: Zhenhuan Zhou, Dalian (CN); Yanxia Feng, Dalian (CN); Xinsheng Xu, Dalian (CN); Jiabin Sun, Dalian (CN); Qilin Zhang, Dalian (CN); Qianshou Qi, Dalian (CN); CheeWah Lim, Dalian (CN)

(73) Assignee: DALIAN UNIVERSITY OF TECHNOLOGY, Dalian (CN)

( * ) Notice: Subject to any disclaimer, the term of this patent is extended or adjusted under 35 U.S.C. 154(b) by 0 days.

(21) Appl. No.: 17/990,231

(22) Filed: Nov. 18, 2022

(65) Prior Publication Data

US 2023/0173307 A1 Jun. 8, 2023

(30) Foreign Application Priority Data

Dec. 6, 2021 (CN) .......................... 202111480826.9

(51) Int. Cl.
*A61N 7/00* (2006.01)
*A61B 8/00* (2006.01)
(Continued)

(52) U.S. Cl.
CPC .............. *A61N 7/00* (2013.01); *A61B 8/4281* (2013.01); *A61B 8/4444* (2013.01);
(Continued)

(58) Field of Classification Search
CPC ... A61B 8/4281; A61B 8/4444; A61B 8/4483; B06B 1/0622; A61N 7/00
See application file for complete search history.

(56) References Cited

U.S. PATENT DOCUMENTS 8,050,430 B2 * 11/2011 Jiang .................... H04R 23/002
381/164
2011/0215673 A1 * 9/2011 Lan ........................ H02N 10/00
310/306
(Continued)

FOREIGN PATENT DOCUMENTS

CN 101715160 A 5/2010
CN 102189073 A 9/2011
(Continued)

*Primary Examiner* — J. San Martin
(74) *Attorney, Agent, or Firm* — Muncy, Geissler, Olds & Lowe, P.C.

(57) ABSTRACT

A flexible variable frequency ultrasonic therapeutic probe based on thermoacoustic effect of a carbon nanotube film comprises an ultrasonic sound production element, and a heat dissipation layer and an acoustic matching layer located on both sides thereof. The sound production element comprises a carbon nanotube film, metal electrodes and wires, and the shape and size of the sound production element can be adjusted according to the actual functional requirements. When a signal is accessed into the sound production element, the carbon nanotube film produces a corresponding temperature change, which causes the surrounding media to expand and contract and to excite ultrasonic waves. The present invention greatly improves the coupling efficiency between the probe and the subject, reduces the energy loss of ultrasonic waves, and enhances the uniformity of the sound intensity distribution in the affected part.

4 Claims, 1 Drawing Sheet

(51) Int. Cl.
  *B06B 1/06*    (2006.01)
  *G10K 11/02*   (2006.01)
(52) U.S. Cl.
  CPC ............ *A61B 8/4483* (2013.01); *A61B 8/546* (2013.01); *B06B 1/0622* (2013.01); *G10K 11/02* (2013.01)

(56) References Cited

U.S. PATENT DOCUMENTS

| | | | |
|---|---|---|---|
| 2014/0185840 A1* | 7/2014 | Wei | H04R 23/002 |
| | | | 381/164 |
| 2015/0190116 A1 | 7/2015 | Song | |
| 2017/0164926 A1 | 6/2017 | Spicci et al. | |

FOREIGN PATENT DOCUMENTS

| | | |
|---|---|---|
| CN | 110639783 A | 1/2020 |
| CN | 111820946 A | 10/2020 |
| TW | I500331 B * | 9/2015 |

\* cited by examiner

FLEXIBLE VARIABLE FREQUENCY ULTRASONIC THERAPEUTIC PROBE BASED ON THERMOACOUSTIC EFFECT OF CARBON NANOTUBE FILM

TECHNICAL FIELD

The present invention belongs to the technical field of ultrasonic therapy, and relates to a flexible variable frequency ultrasonic therapeutic probe based on thermoacoustic effect of a carbon nanotube film.

BACKGROUND

Among the existing medical devices, the ultrasound therapeutic device has become an important therapeutic device due to the characteristics of small trauma, environmental protection, convenience, low cost and relative safety. However, the core technology of the ultrasound therapeutic device is mostly monopolized by foreign countries, it is difficult to achieve independent innovation of domestic devices, and the imported ultrasonic therapeutic device is expensive and difficult to be widely used in daily life to meet the actual needs of people. The ultrasonic therapeutic probe is the main component of the ultrasonic medical device, and the frequency range of ultrasonic waves emitted, the energy consumption and the therapeutic precision are directly related to the therapeutic effect. Therefore, it is of great significance for the application of current ultrasound therapeutic devices to design a flexible variable frequency ultrasonic therapeutic probe with low energy and low cost.

The sound production element of the exiting ultrasonic therapeutic probe is mainly made of a piezoelectric material (for example, piezoelectric ceramics, piezoelectric crystal or piezoelectric polymer) and realizes the conversion of electrical energy and sound energy by means of piezoelectric effect. When a signal passes through the piezoelectric material, electric charges will be generated on the surface to form voltage, and the material will deform under the action of the electric field and drive the surrounding media to vibrate, so as to produce sound. The traditional ultrasonic therapeutic probe made of the piezoelectric material has four main disadvantages: (1) The frequency range of ultrasonic waves that can be emitted by the piezoelectric material is very small, so frequency conversion control cannot be realized. (2) The piezoelectric material will vibrate during the sound production process, causing resonance effect, signals between elements will produce crosstalk and then lead to transmission errors or loss of audio signals, and the power loss is serious. (3) The traditional ultrasonic therapeutic probe is composed of a spring, a piezoelectric material, a tapered wedge and a circlip, and has complicated structure and complex production process, which greatly increases the volume and manufacturing cost of the device. (4) For the traditional ultrasonic therapeutic probe, it is often necessary to install all or part of the complicated structure into the probe to support and protect fragile elements, and the interface of the probe is mostly made of a rigid material or a material with unchangeable geometrical shape (for example, crystal or compound such as silicon oxide and boron nitride), so it is difficult to achieve close fitting with the complex surface of the subject, which results in nonuniform sound field distribution in the affected part and large loss of ultrasonic energy and easily causes local scald or stinging during the therapeutic process.

The carbon nanotube film has extremely low specific heat capacity per unit area and impedance, and can rapidly generate and release heat energy to the surrounding media when driven at low pressure, leading to the vibration of the media so as to produce ultrasonic waves which have the advantages of wide frequency range, flat frequency response curve and high sound pressure. The carbon nanotube film has favorable flexibility and extensibility, and the shape and size thereof can be cut and made according to the actual requirements. Therefore, the carbon nanotube film ensures the feasibility thereof as a potential substitute of the traditional piezoelectric sound production material due to excellent thermoacoustic properties and mechanical properties, and also brings possibilities to realize a flexible ultrasonic therapeutic probe with miniaturization, convenience, high conversion efficiency, good flexibility and variable frequency.

SUMMARY

In view of the problems in the prior art, the present invention provides an ultrasonic therapeutic probe with a carbon nanotube film, which can produce ultrasonic waves with wide frequency range to realize the function of frequency conversion and has the advantages of no vibration element, simple structure and low production cost; and the probe has favorable flexibility and can be closely fitted to the complex surface of the subject, so as to improve the coupling efficiency between the probe and the subject, reduce the energy loss of ultrasonic waves, and enhance the uniformity of sound intensity distribution in the affected part.

To achieve the above purpose, the present invention adopts the following technical solution:

A flexible variable frequency ultrasonic therapeutic probe based on thermoacoustic effect of a carbon nanotube film, comprising an ultrasonic sound production element, and a heat dissipation layer and an acoustic matching layer located on both sides thereof; and both ends of a carbon nanotube film are respectively connected with a metal electrode, and each metal electrode is connected with a wire to constitute the ultrasonic sound production element, wherein the wire is connected with an external device or power supply, one wire is used as an information input end, and the other wire is used as a signal output end. The heat dissipation layer and the acoustic matching layer are arranged on both sides of the carbon nanotube film, wherein the heat dissipation layer is used to dissipate and uniformly distribute heat accumulated on the surface of the film so as to avoid scald to the contact surface caused by high temperature accumulated on the surface of the film, and the acoustic matching layer is fitted to the surface of the subject, with the acoustic impedance set between that of the ultrasonic sound production element and of the subject, for matching the acoustic resistance of the ultrasonic sound production element and the subject, so as to reduce the energy loss of ultrasonic waves emitted by the ultrasonic sound production element.

A signal is accessed into the sound production element by one wire through one metal electrode and then output by the other wire through the other metal electrode, and when the signal flows through the carbon nanotube film, the surface of the film rapidly produces a corresponding temperature change, which causes the surrounding environmental media to expand and contract and to excite ultrasonic waves with wide bandwidth. The flexible ultrasonic therapeutic probe with a carbon nanotube film can produce ultrasonic waves with wide frequency range to realize the function of frequency conversion, so as to be used for therapy of tissues with different depths of the subject.

Further, the carbon nanotube film is composed of carbon nanotubes arranged in the same direction, and the arrangement direction of the carbon nanotubes is parallel to the surface of the film; and the metal electrodes are connected to both ends of the carbon nanotube film in the arrangement direction, and the carbon nanotube film is tensioned after being connected with the metal electrodes.

Further, the carbon nanotube film can be made into a square, circular or annular shape according to the actual requirements.

Further, the metal electrodes and the carbon nanotube film are connected and fixed by conductive binder.

Further, the metal electrodes can be made of a conductive material such as copper sheet or copper wire with low resistivity and favorable flexibility.

Further, the wire and the metal electrode are connected by means of welding with a welding tool.

Further, the heat dissipation layer is pasted on one side of the carbon nanotube film and can be made of a flexible heat dissipation material with insulativity, high temperature resistance and favorable thermal conductivity, such as thermally conductive silicone grease, thermally conductive adhesive tape and thermally conductive graphite film.

Further, the acoustic matching layer is pasted on the other side of the carbon nanotube film opposite to the heat dissipation layer and can be made of a flexible material with insulativity, high temperature resistance and resistance to damage and aging, such as rubber film, plastic film and high molecular film.

Further, the electrical signal of the external device or power supply is accessed into the carbon nanotube film by one wire through one metal electrode, and then output by the other wire through the other metal electrode.

The present invention has the following beneficial effects:

(1) Compared with the sound production material of the traditional ultrasonic therapeutic probe, the carbon nanotube film, as the sound production material of the ultrasonic therapeutic probe, can emit ultrasonic waves with wide frequency range to realize the function of frequency conversion.

(2) The carbon nanotube film does not vibrate when producing sound as the sound production element, which will not lead to crosstalk and loss of signals. Compared with the traditional ultrasonic therapeutic probe made of a piezoelectric material, the probe has low power consumption and stable signals.

(3) Because the sound production element of the ultrasonic therapeutic probe only comprises the carbon nanotube film, the probe has simple structure, simple manufacturing process and low production cost, which is conducive to realization of the miniaturization and convenience of the ultrasonic therapeutic probe.

(4) Unlike those of the traditional hard probe, the elements of the probe are made of flexible materials with certain strength, so the elements do not need to be encapsulated in the hard shell. The acoustic matching layer can be closely fitted to the surface of the subject directly, so as to greatly improve the coupling efficiency between the probe and the subject, reduce the energy loss of ultrasonic waves, and enhance the uniformity of sound intensity distribution in the affected part.

In the figures: 1 carbon nanotube film; 2 metal electrode A; 3 metal electrode B; 4 wire A; 5 wire B; 6 heat dissipation layer; and 7 acoustic matching layer.

DETAILED DESCRIPTION

The present invention is further described below in combination with specific embodiments.

Figure 1:
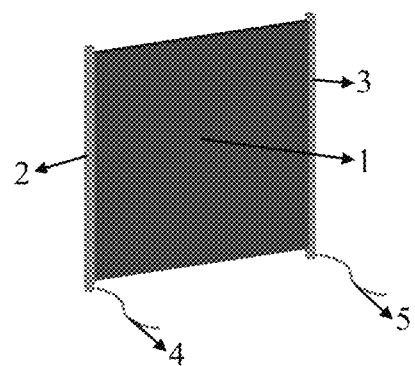
FIG. 1 is a schematic diagram of a sound production element of an ultrasonic therapeutic probe with a carbon nanotube film.
Figure 2:
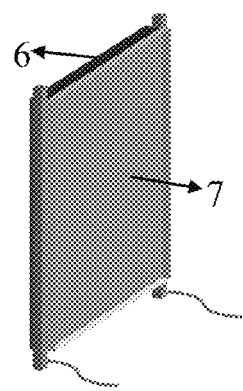
FIG. 2 is a schematic diagram of an ultrasonic therapeutic probe with a carbon nanotube film.

FIG. 1 is a structural schematic diagram of a sound production element of an ultrasonic therapeutic probe with a carbon nanotube film. FIG. 2 is a structural schematic diagram of an ultrasonic therapeutic probe with a carbon nanotube film. The sound production element comprises a carbon nanotube film 1, a metal electrode A 2, a metal electrode B 3, a wire A 4 and a wire B 5. The ultrasonic therapeutic probe with a carbon nanotube film comprises a sound production element, and a heat dissipation layer 6 and an acoustic matching layer 7 located on both sides thereof. Both ends of the carbon nanotube film 1 along the arrangement direction of carbon nanotubes are respectively connected with the metal electrode A 2 and the metal electrode B 3; the wire A 4 is connected with the metal electrode A 2 by means of welding, and the wire B 5 is connected with the metal electrode B 3 by means of welding; the heat dissipation layer 6 and the acoustic matching layer 7 are respectively pasted on both sides of the carbon nanotube film 1, and the carbon nanotube film 1, the heat dissipation layer 6 and the acoustic matching layer 7 are kept in a tensioned state; and a signal is accessed into the sound production element through the wire A 4 and the wire B 5 so that the flexible ultrasonic therapeutic probe with a carbon nanotube film outputs ultrasonic waves with wide bandwidth to realize the function of frequency conversion.

The carbon nanotube film 1 is composed of carbon nanotubes connected end to end and can be cut and made into a square, circular or annular shape according to the actual requirements. The metal electrode A 2 and the metal electrode B 3 are both made of a flexible solid metal conductor with low resistivity and fixedly connected with both ends of the carbon nanotube film 1 along the arrangement direction of carbon nanotubes by binder respectively. The wire A 4 and the wire B 5 are both made of a metal material and respectively connected with the electrode 2 and the electrode 3 by means of welding, and a signal is accessed into the sound production element through the wires. The heat dissipation layer 6 is made of a flexible heat dissipation material with insulativity, high temperature resistance and favorable thermal conductivity and can be cut and made into the same shape and size as the carbon nanotube film 1. The acoustic matching layer 7 is made of a flexible material with matching acoustic impedance and certain strength and can be cut and made into the same shape and size as the carbon nanotube film 1.

In the embodiments of the present invention, the carbon nanotube film 1 of the sound production element is square with a side length of 30 mm and a thickness of 0.025 mm; the metal electrode A 2 and the metal electrode B 3 are made of a thin copper sheet; the wire A 4 and the wire B 5 are made of copper; the heat dissipation layer 6 is a square copper foil graphene heat radiation fin with a side length of 3 cm, a thermal conductivity of 1500 W/m·K and a thickness of 0.1 mm; and the acoustic matching layer 7 is a square polydimethylsiloxane (PDMS) film with a side length of 30 mm, an acoustic impedance of 1500 W/m·K and a thickness of 0.025 mm. Epoxy conductive adhesive (SINWE6529) is evenly applied to the joint of the electrode 2, the electrode 3 and the carbon nanotube film 1, and then the metal electrode A 2, the metal electrode B 3 and the carbon nanotube film 1 are aligned, joined together and compacted. After 24 h, the adhesive is completely cured to realize the fixed connection of the metal electrodes and the film. The wire A 4 and the wire B 5 are respectively welded on the metal electrode A 2 and the metal electrode B 3 by an electric soldering iron. The heat dissipation layer 6 is spread and covered on the surface of one side of the carbon nanotube film 1, and the aligned edges are pasted and fixed with ultraviolet curing adhesive (ergo8500). The acoustic matching layer 7 is spread and covered on the surface of the other side of the carbon nanotube film 1 opposite to the heat dissipation layer 6, and the aligned edges are pasted and fixed with ultraviolet curing adhesive (ergo8500).

In the embodiment, the temperature rise of the ultrasonic therapeutic probe is tested under normal conditions in accordance with GB/T 36419-2018. The ambient temperature is room temperature of 20° C., the input power is 1 W, the acoustic frequency is 30,000 Hz, and the test point is located 10 mm away from the central axis of the surface of the acoustic matching layer of the ultrasonic therapeutic probe. An infrared thermal imager (FLUKE TIS55+) is used to measure that the maximum surface temperature of the acoustic matching layer of the ultrasonic therapeutic probe is 40.2° C. after power-on for 5 minutes, which is lower than the maximum temperature (43° C.) that human skin can withstand and also 40° C. lower than the maximum surface temperature of a single carbon nanotube film with the same size and properties under the test conditions, and the surface temperature distribution of the ultrasonic therapeutic probe is more uniform. Therefore, when the ultrasonic therapeutic probe has high input power, the maximum surface temperature is still lower than the maximum temperature that human skin can withstand, which ensures that the ultrasonic therapeutic probe can be directly fitted to the affected part, and the surface temperature distribution of the ultrasonic therapeutic probe is uniform, which avoids local scald.

In the embodiment, according to GB/T 19890-2005, an acoustic measurement platform is built and the ultrasonic therapeutic probe is acoustically tested. The ultrasonic therapeutic probe is placed in a water tank with de-aerated water, a hydrophone (B&K8103) is used to measure the output sound pressure in the plane state and in the curved state with the curvature radius of 10 mm, 15 mm and 20 mm respectively, and the de-aerated water in the water tank is more than 30 cm above the hydrophone to reduce the influence of acoustic reflection of the liquid level on the measurement result. The input power is 1 W, and the test point is located 10 mm away from the central axis of the surface of the acoustic matching layer of the ultrasonic therapeutic probe. Within the frequency range of 0 to 60,000 Hz, ultrasonic waves produced by the ultrasonic therapeutic probe in the plane state and in the curved state with the curvature radius of 10 mm, 15 mm and 20 mm respectively have wide frequency range and flat frequency response curve, with the sound intensity meeting the range of therapeutic ultrasonic waves (with the sound intensity less than 3 W/cm$^2$), and the levels of sound pressure output in the plane state at various frequencies and in the curved state with different curvatures only differ by ±5 db. Therefore, the flexible ultrasonic therapeutic probe can be closely fitted to complex surfaces and can produce ultrasonic waves with wide frequency range and high sound pressure when fitted to surfaces with different curvatures.

The above embodiments only express the implementation of the present invention, and shall not be interpreted as a limitation to the scope of the patent for the present invention. It should be noted that, for those skilled in the art, several variations and improvements can also be made without departing from the concept of the present invention, all of which belong to the protection scope of the present invention.

The invention claimed is:

1. A flexible variable frequency ultrasonic therapeutic probe based on thermoacoustic effect of a carbon nanotube film, wherein the flexible variable frequency ultrasonic therapeutic probe comprises an ultrasonic sound production element, and a heat dissipation layer and an acoustic matching layer respectively located on two sides of the ultrasonic sound production element; the ultrasonic sound production element includes a carbon nanotube film and conductive metal electrodes respectively located on two ends of the carbon nanotube film, wherein each metal electrode is connected with a wire, the wire is used for connecting an external device or power supply, one wire is used as an signal input end, and the other wire is used as a signal output end; the heat dissipation layer and the acoustic matching layer are respectively arranged on two sides of the carbon nanotube film, and the acoustic matching layer is fitted to a surface of a subject, with the acoustic impedance of the acoustic matching layer set between that of the ultrasonic sound production element and of the subject; and a signal is input into the sound production element though the signal input end and output by the signal output end, and when the signal flows through the carbon nanotube film, a surface of the carbon nanotube film rapidly produces a temperature change, which causes the surrounding environmental media to expand and contract and to excite ultrasonic waves with wide bandwidth;

the carbon nanotube film includes carbon nanotubes arranged in a first direction, and the first direction of the carbon nanotubes is parallel to a second direction along which the surface of the carbon nanotube film is extended;

the metal electrodes are respectively connected to two ends of the carbon nanotube film in the first direction, and the carbon nanotube film is tensioned after being connected with the metal electrodes.

2. The flexible variable frequency ultrasonic therapeutic probe based on thermoacoustic effect of a carbon nanotube film according to claim 1, wherein the metal electrodes and the carbon nanotube film are connected and fixed by conductive binder.

3. The flexible variable frequency ultrasonic therapeutic probe based on thermoacoustic effect of a carbon nanotube film according to claim 1, wherein the heat dissipation layer is pasted on one side of the carbon nanotube film and made of a flexible heat dissipation material.

4. The flexible variable frequency ultrasonic therapeutic probe based on thermoacoustic effect of a carbon nanotube film according to claim 1, wherein the acoustic matching layer is pasted on the other side of the carbon nanotube film, opposite to the heat dissipation layer, and is made of a flexible material.

* * * * *